| United States Patent [19] | [11] Patent Number: 4,687,666 |
|---|---|
| O'Daly | [45] Date of Patent: Aug. 18, 1987 |

[54] VACCINE FOR LEISHMANIASIS

[75] Inventor: Jose A. O'Daly, Caracas, Venezuela

[73] Assignee: Ministerio de Sanidad y Asistencia Social Instituto Venezolano de Investigationes Cientificas, Caracas, Venezuela

[21] Appl. No.: 703,176

[22] Filed: Feb. 19, 1985

[51] Int. Cl.$^4$ .................. A61K 39/008; C12N 1/10
[52] U.S. Cl. ............................. 424/88; 435/258
[58] Field of Search ............... 435/68, 240, 258; 424/88, 93

[56] References Cited

PUBLICATIONS

Poulter, Clin. Exp. Immunol., vol. 36, pp. 30–37, 1979.
Poulter, Clin. Exp. Immunol., vol. 39, pp. 14–26, 1980.
Poulter et al., Clin. Exp. Immunol, vol. 42, pp. 211–218, 1980.
Zuckerman, Exp. Parasitol., vol. 38, pp. 370–400, 1975.
Poulter, Cellular Immunity, vol. 27, pp. 17–25, 1976.
Merck Index, p. 1043, 1983.
Urckerman, Biology of the Kinetoplastida, pp. 1–34.
O'Daly et al., Experiment Parasitology, vol. 47, pp. 221–231, 1979.
Glazer, J. Biol. Chem., vol. 242, pp. 433–436, 1967.
Rushizky et al., Biochem. Biophys. Res. Comm., vol. 10, pp. 311–314, 1963.
Ottesen et al., Methods in Enzymology, vol. XIX, pp. 199–215, 1970.
Welbans et al., Advances in Parasitology, vol. 16, pp. 1–33, 1978.
Holbrook, T., et al., Am. J. Trop. Med. Hyg., vol. 30, pp. 762–768, 1981.
Greenblatt, C. et al., J. Biol. Stand., vol. 8, pp. 227–232, 1980.
Green, M., et al., Parasite Immunology, vol. 5, pp. 337–344, 1983.

*Primary Examiner*—Blondel Hazel
*Attorney, Agent, or Firm*—Browdy and Neimark

[57] ABSTRACT

Mammals immunized with an innoculum containing TLCK-treated and killed Leishmania cells show an increased resistance to Leishmaniasis.

8 Claims, 7 Drawing Figures

VACCINE FOR LEISHMANIASIS

FIELD OF THE INVENTION

This invention relates generally to vaccines against protozoa and specifically Leishmaniasis caused by the Leishmania genus, especially *Leishmania brasiliensis* (LB) and *Leishmania donovani* (LD).

BACKGROUND OF THE INVENTION

The first of the above named parasites is the agent of a disease named mucotaneous leishmaniasis; the second parasite is the agent of visceral leishmaniasis or Kalaazar. Human leishmaniasis are caused by at least 13 different species and subspecies of parasite of the genus Leishmania. The parasites are transmitted to man from other infected human beings or infected vertebrates by sandflies when while the sandflies are taking a blood meal. Leishmaniasis has been reported from about 80 countries and probably some 400,000 new cases occur each year. Recently, the World Health Organization reported 200 million people affected by the disease.

Visceral leishmaniasis is usually fatal if untreated and mucocutaneous leishmaniasis of the New World produces multilation by destruction of the naso-oropharyngeal cavity and in some cases death. Since control of the zoonosis of the New World is quite difficult, the only approach to prevent lesions is early diagnosis and radical treatment of patients since drugs are rather unsatisfactory at the present time.

Various types of vaccines have used:
(1) live parasites (Berverian, 1939, Trans. R. Soc. Trop. Med. Hyg. 33: 87-94; Koufman et al., 1978, Isr. Med. Sci. 14:218-222);
(2) frozen promastigotes from culture (Witztum et al., 1979, Isr. J. Med. Sci. 15: 749-73);
(3) sonicated promastigotes (Beacham et al., 1982, Am. J. Trop. Med. Hyg. 31: 252-258);
(4) gamma-irradiated live promastigotes (Howard et al., 1982, J. Immunol. 129: 2206-2212);
(5) formalin-killed promastigotes treated with glucan (Holbrook et al., 1981, Am., J. Trop. Med. Hyg. 30: 762-768).

However, none of the above vaccines have given satifactory results. Only the first and second ones have been applied to human. Since the parasites are alive, the immunity is the consequence of an infection and not the result of vaccination with non-infective parasites.

SUMMARY OF INVENTION

It is an object of this invention to provide immunity to vertebrate mammals against diseases caused by protozoa of the Leishmania genus.

It is another object of this invention to provide immunity to vertebrate mammals against leishmaniasis employing a vaccine containing killed leishmaia protozoa.

It is a further object of this invention to provide immunity to vertebrate mammals against diseases caused by *Leishmania brasiliensis*, *L. donovani chagasi* and *L. donovani*.

These and other objects are achieved according to the present invention. Organisms of the genus Leishmania are cultivated in the promastigote state in an appropriate synthetic culture medium supplemented with about 10% fetal bovine serum typically at about 30° C. The organisms are then collected at the stationary phase and washed. The cultivated organisms are then incubated in a medium, for example, Eagle's minimal medium, which contains an amount of TLCK (a proteolytic enzyme inhibitor) sufficient to kill the organisms (TLCK does not lyse the cells). The killed organisms are then separated from the incubation medium and an innoculum formed therefrom.

A similar method may also be effective to create vaccines against other protozoans. The preferred genus is Leishmania and the most preferred species are *L. brasiliensis* and *L. donovani*.

DETAILED DESCRIPTION OF THE PREFERRED EMBODIMENT

The hamster was chosen as an animal model because it is most susceptible to both types of visceral and mucocutaneous leishmaniasis and is widely used to isolate species of Leishmania from wild rodents and human beings.

Correspondingly, both diseases in the infected hamster and then the cure that the animals experience once they are vaccinated with the antigenic preparations prior to infection with virulent parasites will be described. One sensitive and accurate way to follow infection is through the analysis of the lymphocyte response to T and B cell mitogens. Briefly, the lymphocyte response was assayed as follows:

Blastogenesis assay: $2 \times 10^5$ mononuclear splenic cells/well (Falcon #3040) in a volume of 100 ul of RPMI-1640 supplemented with 5% fetal bovine serum (FBS, GIBCO) penicillin (100 units/ml), streptomycin (100 micrograms/ml) and 25 mM HEPES (Sigma) were used for each assay. Cells were incubated at 37° C. in 5% $CO_2$ for 48 hours after which 0.2 uCi of $^3H$-thymidine (2.5 ci/mmol., New England Nuclear, Boston Mass.), was added to each well and incubated for a further 18 hr until the time of harvest. The ability of spleen cells to proliferate in response to mitogens was assessed by adding suboptimal, optimal and supraoptimal doses of Concanavalin A (ConA, 0.5, 1.0 and 2.5 micrograms/ml, Sigma); Dextran sulphate (DS, 5, 10, and 25 micrograms/ml, Sigma) and Pokeweed mitogen (PWM, 0.5, 1.0 and 2.0%, GIBCO).

Figure 1:
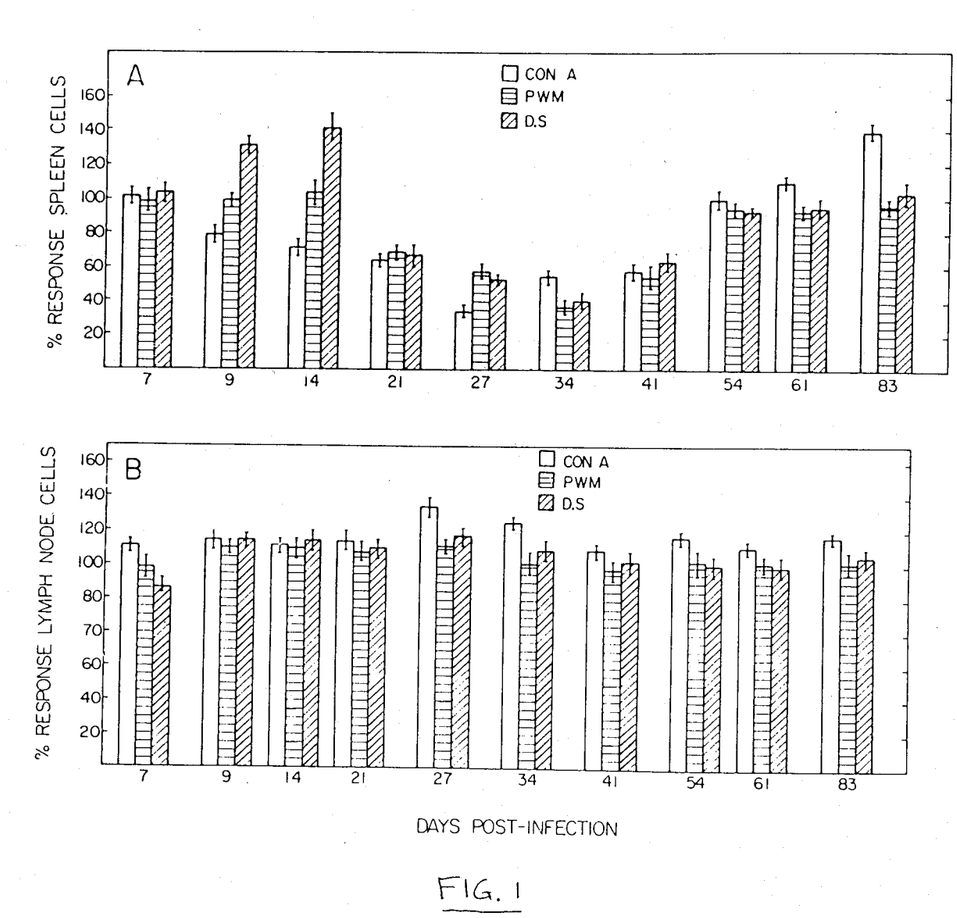
FIG. 1, Blastogenic response to ConA, DS and PWM exhibited by splenic and lymph node lymphocytes from hamsters infected with $10^5$ amastigote forms of *L. donovani* at different times post-infection. Each value represents the average of triplicates of 9 different experiments (9 animals)±standard deviation. Each day had its own control value. Control values (average of 30 animals, 1 animal per day post-infection, per experiment) for:
(1) Spleen cells: ConA=45,691±1,210 cpm; PWM=16,206±1,319 cpm; DS=6,098±875;
(2) Lymph node cells: ConA=51,585±2,767 cpm; PWM=12,867±2,464 cpm; DS=6,582±700; In A $P_{21}$, $P_{27}$, $P_{34}$ less than 0.01 vs control.
Figure 2:
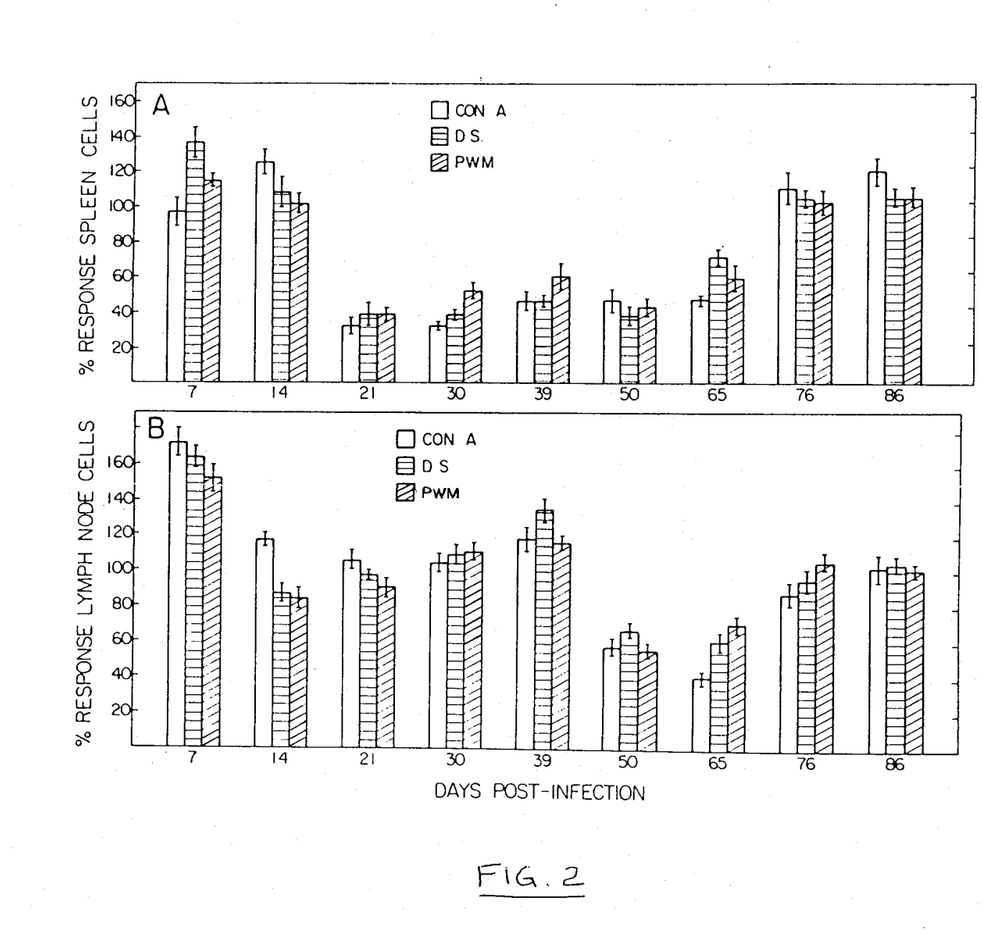
FIG. 2, Blastogenic response to ConA, DS and PWM exhibited by splenic and lymph node lymphocytes from hamsters infected with $10^5$ amastigote forms of *L. brasiliensis* at different times post-infection. Each value presents the average of triplicates of 9 different experiments±standard deviation (9 animals). Each day had its own control value. Control value (average of 30 animals, 1 animal per day of infection per experiment) for:
(1) Spleen cells: ConA=42,923±1,100 cpm; PWM=16,109±1,212 cpm; DS=6,611±658 cpm. The P values versus control for mitogens responsiveness in A at 21, 30, 39, 50 and 65 days post-infection. In B, at 7 days for all mitogens P was less than 0.01; for DS and PWM P was less than 0.05; at 39 days for all mitogens P was less than 0.05; at 50 and 65 days for all mitogens P was less than 0.01.

Cultures were processed with a multiple automated cell harvester (M24, Brandell, Gaithersburg, MD). After drying, the glass fiber discs (Reeve Angel, grade 934, AH, CURTIN) were placed in vials with Packard scintillation fluid and then counted. Results are expressed as % response, calculted as $(E_1-C_1/E_2-C_2) \times 100$. $E_1$=cpm infected cells+mitogens; $C_1$=cpm infected cells; $E_2$=cpm normal cells+mitogens; $C_2$=cpm normal cells. Each value represents the average of triplicates of nine different experiments (9 animals)±standard deviation. For each experimental point on the curve a normal control was set up from animals matched for weight and age. The P next to the sub-index in each figure corresponds to the probabilities versus control according to Student's t test at each day post-infection. The animals infected with $10^5$ virulent amastigotes obtained from the spleen of a hamster infected with *L. donovani* exhibited immunosuppression of spleen lymphocytes between 21 and 41 days post-infection. Lymph node cells however, responded as normal cells to mitogens stimulation (FIG. 1). The animals infected with $10^5$ *L. brasiliensis* amastigotes obtained from the nodules of infected hamsters (see FIG. 7) presented immunosuppression of spleen cells from day 21–65 post-infection and of lymph node cells from day 14 to 21 and 50 to 65 post-infection (FIG. 2).

IMMUNIZATION OF THE ANIMALS

*L. brasiliensis* promastigotes were grown at 30° C. in a synthetic culture medium containing the ingredients listed in Table I, supplemented with 5% FBS. The cultured cells are then collected at the stationary phase of growth and washed three times with PBS, pH 7.5 by centrifugation at $900 \times g$ for 15 mins. at 4° C.

TABLE 1

| Ingredient | mg/lt | Ingredient | mg/lt |
|---|---|---|---|
| Methionine | 140 | Carnosine | 35 |
| Tryptophan | 50 | Citrulline | 50 |
| α-Amino Adipic Acid | 3 | Sarcosine | 57 |
| Asparagine | 165 | $CaCl_2$ | 200 |
| Anserine | 17 | $Fe(NO_3)9H_2O$ | 0.72 |
| Cystine | 47 | KCl | 400 |
| Histidine | 6 | $MgSO_4\ 7H_2O$ | 200 |
| Aspartic Acid | 120 | NaCl | 6,800 |
| Alanine | 512 | $NaHCO_3$ | 2,200 |
| Proline | 248 | $NaH_2PO_4.H_2O$ | 140 |
| Lysine | 337 | Tricine | 900 |
| Taurine | 6 | Hemin | 1 |
| Isoleucine | 191 | HEPES | 2,340 |
| Ornithine | 3 | Glucose | 1,000 |
| Tyrosine | 210 | D-ribose | 10 |
| β-alanine | 80 | 2-Deoxy-ribose | 10 |
| Phosphoserine | 23 | Cholecalciferol ($D_3$) | 0.1 |
| α-amino Butyric Acid | 8 | | |
| Leucine | 440 | Biotin | 1 |
| Arginine | 413 | Pyridoxamine | 0.05 |
| Serine | 220 | Pyridoxal | 1 |
| Hydroxylysine | 12 | Cyanocobalamin ($B_{12}$) | 0.01 |
| Glutamine | 164 | | |
| Glutamic Acid | 420 | Choline | 1 |
| Cysteine | 0.5 | Thiamine ($B_1$) | 1 |
| Phosphoethanolamine | 30 | Inositol | 2 |
| Threonine | 200 | α-Tocopherol | 0.01 |
| Glycine | 235 | 3-phytylmenadione ($K_1$) | 0.01 |
| Phenylalanine | 140 | | |
| Valine | 266 | Menadione ($K_3$) | 0.01 |
| d-Pantothenic Acid | 1 | Retinol (A) | 0.14 |
| Ascorbic Acid | 0.05 | Riboflavin ($B_{12}$) | 0.1 |
| p-Aminobenzoic Acid | 0.05 | 6, 8 Thiotic Acid | 0.01 |
| Ergocalciferol ($D_2$) | 0.1 | Pyridoxine ($B_6$) | 0.025 |
| Folic Acid | 1 | | |
| Niacinamide | 1 | | |
| L-carnitine | 0.05 | | |
| DL-methionine-S—methyl-sulfonium chloride (U) | 0.05 | | |
| Deoxycitidylic Acid (d-CMP) | 3.51 | | |
| Adenosine-5'-Triphosphate (ATP) | 5.51 | | |
| 2'Deoxyadenylic Acid (d-AMP) | 3.31 | | |
| Tetrahydrofolic Acid | 0.5 | | |
| 2'Deoxyuridine-5'-mono-phosphate (d-UMP) | 3.52 | | |
| 5'-Thymidylic Acid (TMP) | 3.22 | | |
| 5'-Deoxyguanylic Acid (d-GMP) | 3.41 | | |

In this culture medium, amastigote differention is up to 95–100% at 30° C., as checked by light microscopy and electromicroscopy.

For the immunization, parasites were incubated for 6 days at 30° C. in Eagle's minimal medium (MEM) (Grand Island Biological Co., Grand Island, N.Y.,) containing 0.01 phenyl-methylsulfonyl-fluoride (PMSF, Sigma), Or 150 ug/ml of N-p-Tosyl-1-lysine-chloromethyl ketone, HCL (TLCK) in 2% (v/v) 2-propanol. The PMSF or TLCK was removed by centrifugation at 900×g for 15 mins. at 4° C. No parasite survived these treatments as judged from examination of the cultures and/or infection in inoculated hamsters. One×$10^8$ PMSF-treated or TLCK-treated parasites were inoculated i.p. in hamsters every week for 3 weeks. Seven days after the last dose, the animals were inoculated with $10^5$ amastigotes obtained from nodules of LB-infected animals, or from spleens of LD-infected hamsters as described. Experimental animals were exanguinated by cardiac puncture ether anesthesia. Immediately after removal, each spleen was teased with forceps in RPMI-1640 and the cells adjusted to 2×$10^6$ cells/ml. Lymph node cells were also obtained from the inguinal, axillary and brachial lymph nodes and processed as described for spleen. Blastogenesis assays were performed as described above. Data are expressed as % response. Each point represents the average of replicates of five different experiments (fifteen animals)±standard deviation (SD). For each experimental point in the curve, a normal control was set up using animals matched for weight and age.

Figure 3:
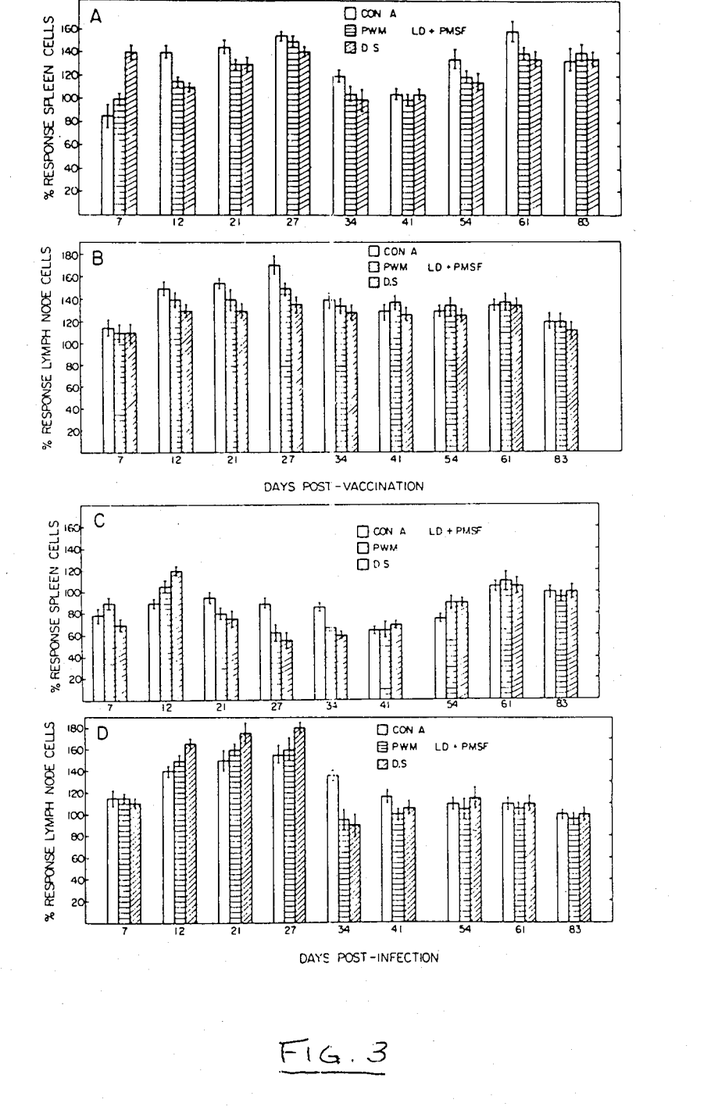
FIG. 3, Blastogenic response to ConA, DS and PWM by splenic and lymph node lymphocytes from hamsters pre-immunized with PMSF-treated LD parasites (A and B) and animal preimmunized with the same preparation but later challenged with $10^5$ LD virulent amastigotes from infected animals (C and D) at different times post-infection. Each value represents the average of triplicates of 15 differents experiments (15 animals)±standard deviation. Each day had its own control value. The values reported for controls are the average of 30 animals. Control values: Spleen cells: ConA=49,951±1,701 cpm; PWM=16,792±1,482 cpm; DS=5,554±742 cpm; DS=5,850±690 cpm.
Figure 4:
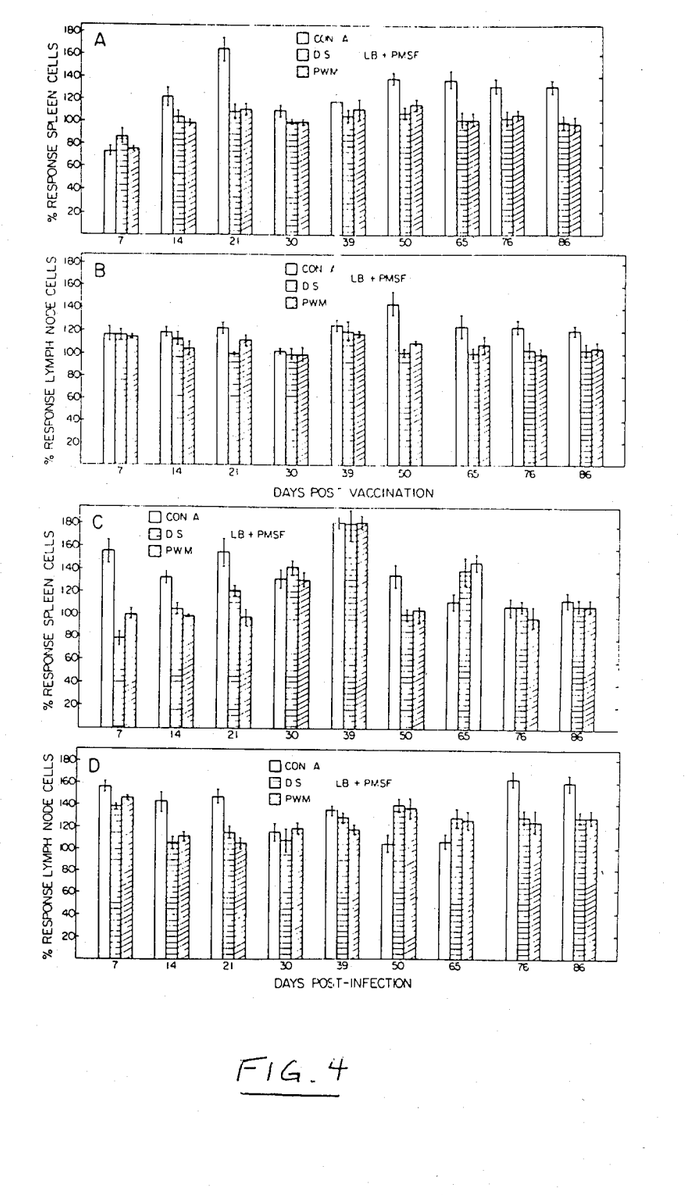
FIG. 4, Blastogenic response to ConA, DS and PWM exhibited by splenic and lymph node lymphocytes from hamsters preimmunized with PMSF-treated LB parasites (A and B) and preimmunized with the same preparation and later challenged with $10^5$ LB amastigotes at different times post-infection (C and D). Each value represents the average of triplicates of 15 animals±standard deviation. Control values are similar to FIG. 6.

Hamsters preimmunized with LD+PMSF showed stimulation of blastogenic response to T and B cell mitogens (FIGS. 3A and B) but spleen cells showed suppression between days 21 and 54 to the mitogen (FIG. 3C) when the animals were infected with $10^5$ virulent LD amastigotes. Lymph node cells from the same animals did not show immunosuppression (FIG. 3D). The same procedure was followed with LB+PMSF treated animals. In these cases, neither vaccinated animals nor vaccinated+$10^5$ LD amastigotes infected animals showed any suppression of the lymphocyte response to mitogens (FIG. 4).

Figure 5:
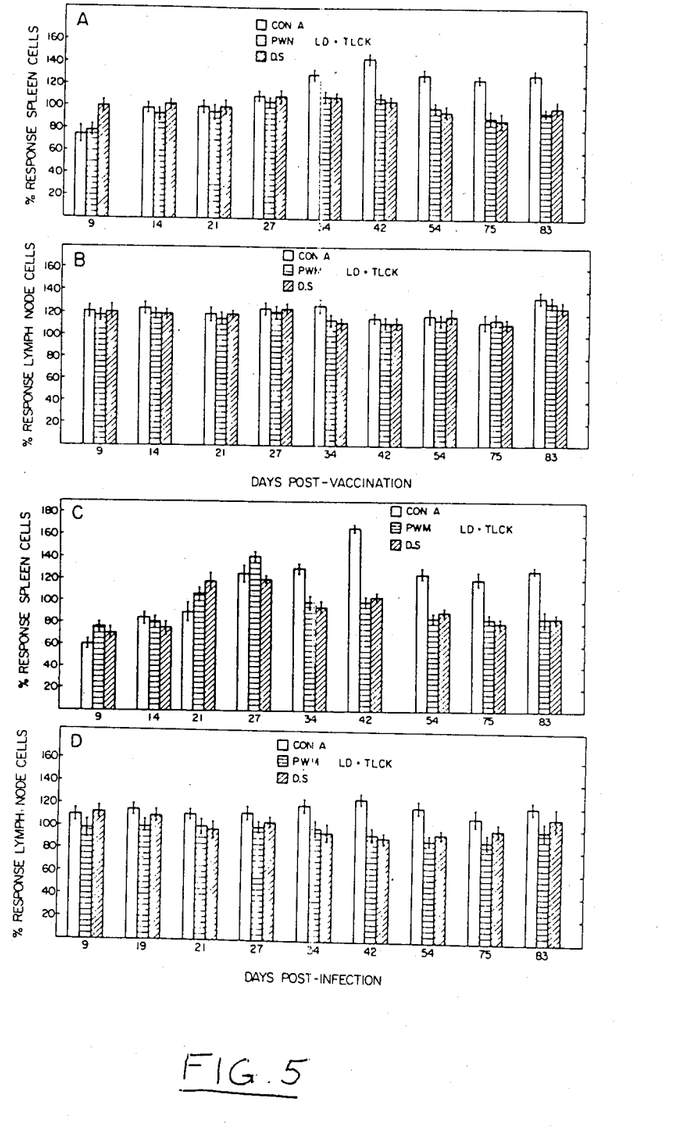
FIG. 5, Blastogenic response to ConA, DS and PWM exhibited by splenic and lymph node lymphocytes from hamsters preimmunized with TLCK-treated LD (A and B) and animals preimmunized with the same preparation but later challenged with $10^5$ LD virulent amastigotes from infected animals (C and D). Each value represents the average of triplicates of 15 different experiments (15 animals)±standard deviation. Control values as in FIG. 3.

Hamsters treated with LD+TLCK presented a better response than LD+PMSF treated animals to mitogens in both vaccinated and vaccinated+$10^5$ LD amastigotes infected animals (FIG. 5).

Figure 6:
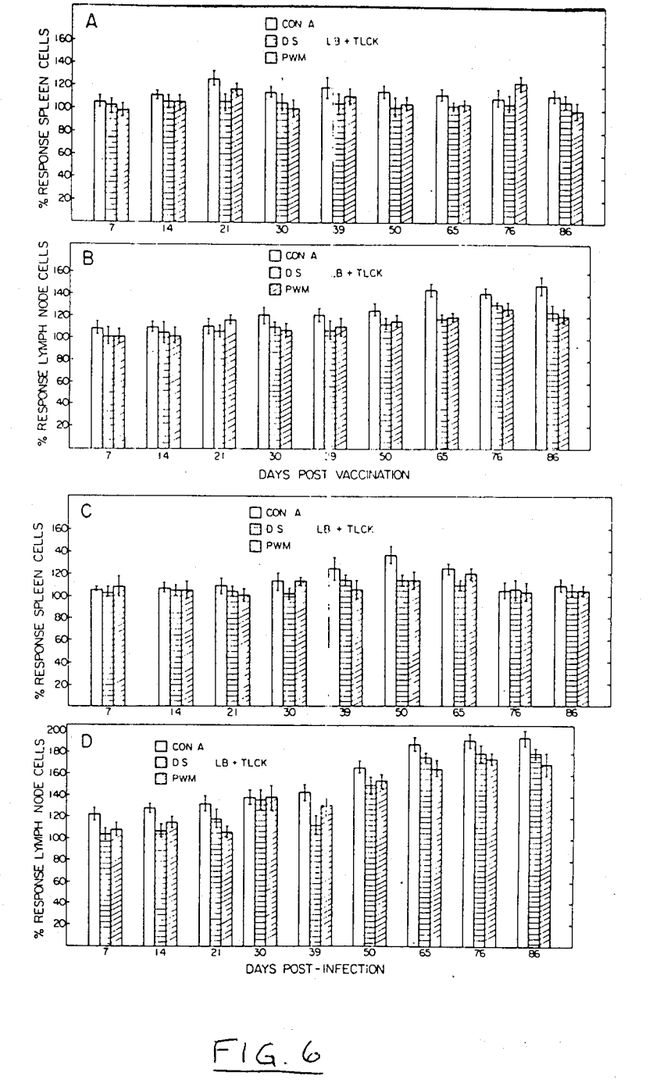
FIG. 6, Blastogenic response to ConA, DS and PWM exhibited by splenic and lymph node lymphocyte from hamsters preimmunized with TLCK treated LB parasites (A and B) and animals preimmunized with the same preparation but later challenged with $10^5$ LD virulent amastigotes from infected animals (C and D) at different times post-infection. Each value represents the average of triplicates of different experiments (15 animals)±standard deviation. Each day had its own control value. The values reported for controls are the average of 30 animals. Control values: Spleen cells: ConA=40,871±1,151 cpm. PWM=15,447±1,628 cpm; DS+6,231±801 cpm; Lymph node cells: ConA=47,383±2,029 cpm; PWM=10,085±1,204 cpm; DS=6,351±815 cpm.

Hamsters treated with LB+TLCK presented stimulation of B and T cells in spleen and lymph nodes in both vaccinated and vaccinated+$10^5$ LB amastigotes infected animals. The latter ones showed stimulation of lymphocyte response in lymph nodes up to 200% of normal uninfected cells which confirms a high degree of protection (FIG. 6).

All the normal animals infected with $10^5$ LD amastigotes or preimmunized with LD+PMSF and infected with $10^5$ LD amastigotes died after 5 months, while the animals preimmunized with LD and TLCK and then infected with $10^5$ LD amastigotes survived more than one year.

Figure 7:
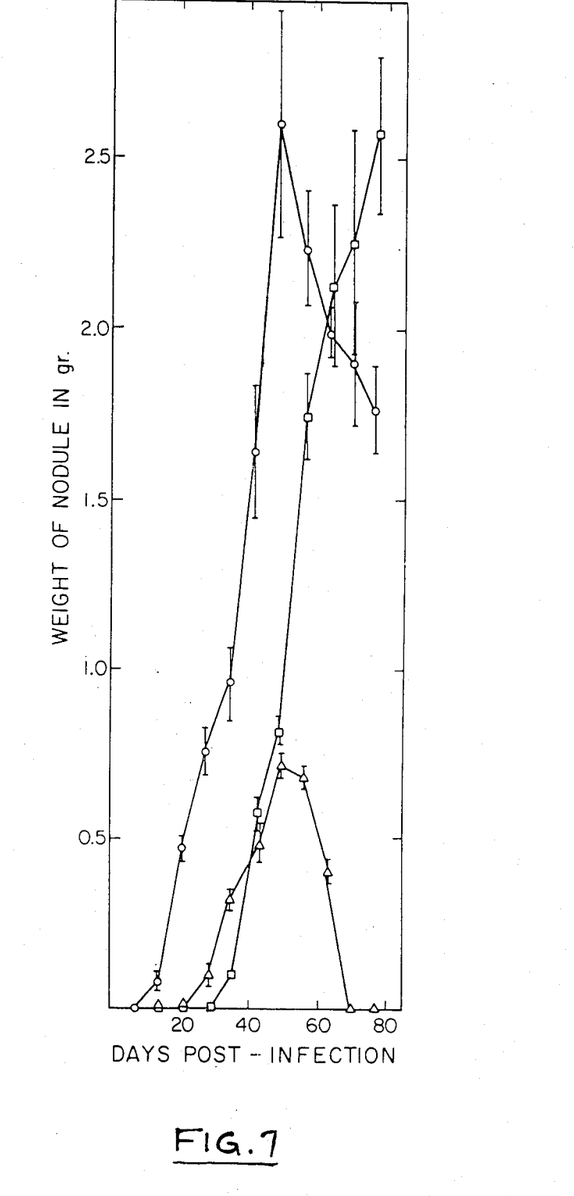
FIG. 7, Weight of nodules from hamsters infected with *L. brasiliensis* with previous immunization with PMSF- or TLCK-treated parasites. Each point is the average of triplicates of three differents experiments (15 animals). The weight of the nodule is presented in unimmunized, infected hamsters (o—o); animals preimmunized with TLCK-treated LB (Δ—Δ), or PMSF-treated LB-(□—□), parasites from culture. All animals were challenged with $10^5$ LB amastigotes.

The evolution of the disease in LB infected animals can be followed by the size of the nodule after $10^5$ LB amastigotes infection at the base of the tail. As shown in FIG. 7, normal animals and LB+PMSF vaccinated animals infected with $10^5$ LB amastigotes showed a nodule that kept growing up to 2.5 gr while LB+TLCK vaccinated and infected animals presented a nodule 4 times smaller than normal unimmunized infected animals that disappeared after 70 days post-infection. Also no lesion was found by careful histopathological study of the site of the infection.

Thus, the TLCK+LB preimmunized and infected hamster was protected as judged by:

1. Normal blastogenic response by splenic lymphocytes throughout the observation period.
2. Absence of parasites in lymph nodes after 56 days.
3. Absence of nodular lesions after 13 weeks whereas in unimmunized LB+PMSF preimmunized or LD+TLCK preimmunized infected hamsters the lesion was still present.
4. Significant recovery of the blastogenic response of lymph node lymphocytes after day 30.

What is claimed is:

1. A vaccine against Leishmaniasis comprising killed cells of the genus Leishmania, said parasites having been killed in the amastigote stage by incubation in vitro at the stationary phase of growth in a medium containing an amount of N-p-tosyl-L-lysine chloromethyl ketone or a pharmacologically acceptable salt thereof effective to kill said cells.

2. The vaccine of claim 1, wherein said cells are *Leishmania donovani* or *Leishmania brasiliensis*.

3. A method for producing a vaccine comprising he steps of:
   subjecting cells of the genus Leishmania, in the amastigote stage, and at the stationary phase of growth, to a medium containing an amount of N-p-tosyl-L-lysine chloromethyl ketone or a pharmacologically acceptable salt thereof effective to kill said cells;
   isolating said killed cells;
   forming an immunostimulating innoculent comprising said killed cells.

4. The method of claim 3 wherein said cells are *Leishmania donovani* or *Leishmania brasiliensis*.

5. A method of immunizing a mammal against leishmaniasis, said method comprising the steps of:
   killing cells of a species of the genus Leishmania by subjecting said cells in the amastigote stage, at the stationary phase of growth, to a medium containing an amount of N-p-tosyl-L-lysine chloromethyl ketone, or a pharmacologically acceptable salt thereof effective to kill said cells;
   isolating said killed cells;
   forming an immunizing innoculum comprising said killed cells
   innoculating said mammal with an amount of said innoculum so as to significantly stimulate the immune system of said mammal against attack from virulent cells of the same species as said killed cells.

6. The method of claim 5 wherein said species is *L. donovani* or *L. brasiliensis*.

7. The method of claim 5 wherein said mammal is innoculated intraperitoneally.

8. The method of claim 7 wherein said mammal is innoculated with a series of doses over a period of less than three weeks.

* * * * *